United States Patent [19]

Klein

[11] Patent Number: 5,869,444
[45] Date of Patent: Feb. 9, 1999

[54] OSMOTIC AGENTS FOR PERITONEAL DIALYSIS

[75] Inventor: Elias Klein, Louisville, Ky.

[73] Assignee: Research Corporation Technologies, Inc., Tucson, Ariz.

[21] Appl. No.: 701,547

[22] Filed: May 15, 1991

Related U.S. Application Data

[60] Division of Ser. No. 182,708, Apr. 18, 1988, Pat. No. 5,039,609, which is a continuation-in-part of Ser. No. 774,261, Sep. 10, 1985, abandoned.

[51] Int. Cl.$^6$ .............................. A01N 37/18; A23C 9/12; C12P 21/06
[52] U.S. Cl. .................... 514/2; 426/41; 426/42; 435/68.1
[58] Field of Search .................. 435/68.1, 272; 514/2; 426/41, 42

[56] References Cited

U.S. PATENT DOCUMENTS

| | | | |
|---|---|---|---|
| 3,061,512 | 10/1962 | Anderson et al. | 514/21 |
| 4,145,455 | 3/1979 | Fujimaki et al. | 426/614 |
| 4,339,433 | 7/1982 | Kartinos et al. | 424/78 |
| 4,427,658 | 1/1984 | Maubois et al. | 424/177 |
| 4,443,540 | 4/1984 | Chervan et al. | 435/69 |
| 4,462,990 | 7/1984 | Jolles et al. | 514/21 |
| 4,574,085 | 3/1986 | Dolkant et al. | 424/680 |
| 4,698,303 | 10/1987 | Bailey et al. | 435/139 |
| 4,801,381 | 1/1989 | Niessen | 210/321.84 |
| 4,847,096 | 7/1989 | Mellqvist et al. | 426/41 |
| 4,906,616 | 3/1990 | Gilchrist et al. | 514/21 |
| 5,039,532 | 8/1991 | Jost et al. | 426/41 |
| 5,112,812 | 5/1992 | Samuelsson | 514/21 |

FOREIGN PATENT DOCUMENTS

| | | |
|---|---|---|
| 0022019 | 1/1981 | European Pat. Off. . |
| 0049666 | 4/1982 | European Pat. Off. . |
| 0065663 | 12/1982 | European Pat. Off. . |
| 2484651 | 11/1980 | France . |
| 2487642 | 2/1982 | France . |
| 8203987 | 11/1982 | WIPO . |
| 83/00087 | 1/1983 | WIPO . |
| 8701286 | 3/1987 | WIPO . |

OTHER PUBLICATIONS

Wood et al. (1974) "Primary Structure of Polypeptides", *Biochemistry: A Problems Approach,* W. A. Benjamin, Inc., Menlo Park, CA, 42, 46–48.

Lehninger (1978) "Partial Hydrolysis of Polypeptide Chains", *Biochemistry,* Worth Publishers, Inc. New York, 106.

Barman (1969) *Enzyme Handbook,* Springer–Verlag, New York, 618–621.

(1972) *Worthington Enzyme Manual,* 122–123.

Nolph, K. et al. (1978) *Trans. Am. Soc. Artif. Intern. Organs* 24: 162–168.

Chemical Abstracts, No. 165635u, vol. 93, No. 17, p. 459, Oct. 27, 1980.

McGary, T.J. et al. (1981) Trans. Am. Soc. Artif. Intern. Organs 27: 314–318.

Klein et al. (1986) *Trans. Am. Soc. Artif. Intern. Organs,* 32, 550–553.

*Primary Examiner*—Jon P. Weber
*Attorney, Agent, or Firm*—Scully, Scott, Murphy & Presser

[57] ABSTRACT

This invention relates to a peritoneal dialysis solution which comprises as an osmotically active agent an osmotically effective amount of a mixture of peptides, the mixture consisting substantially of peptides having a molecular weight of about 300 to about 2000 daltons, and an equivalent weight between about 150 to about 1500.

27 Claims, 7 Drawing Sheets

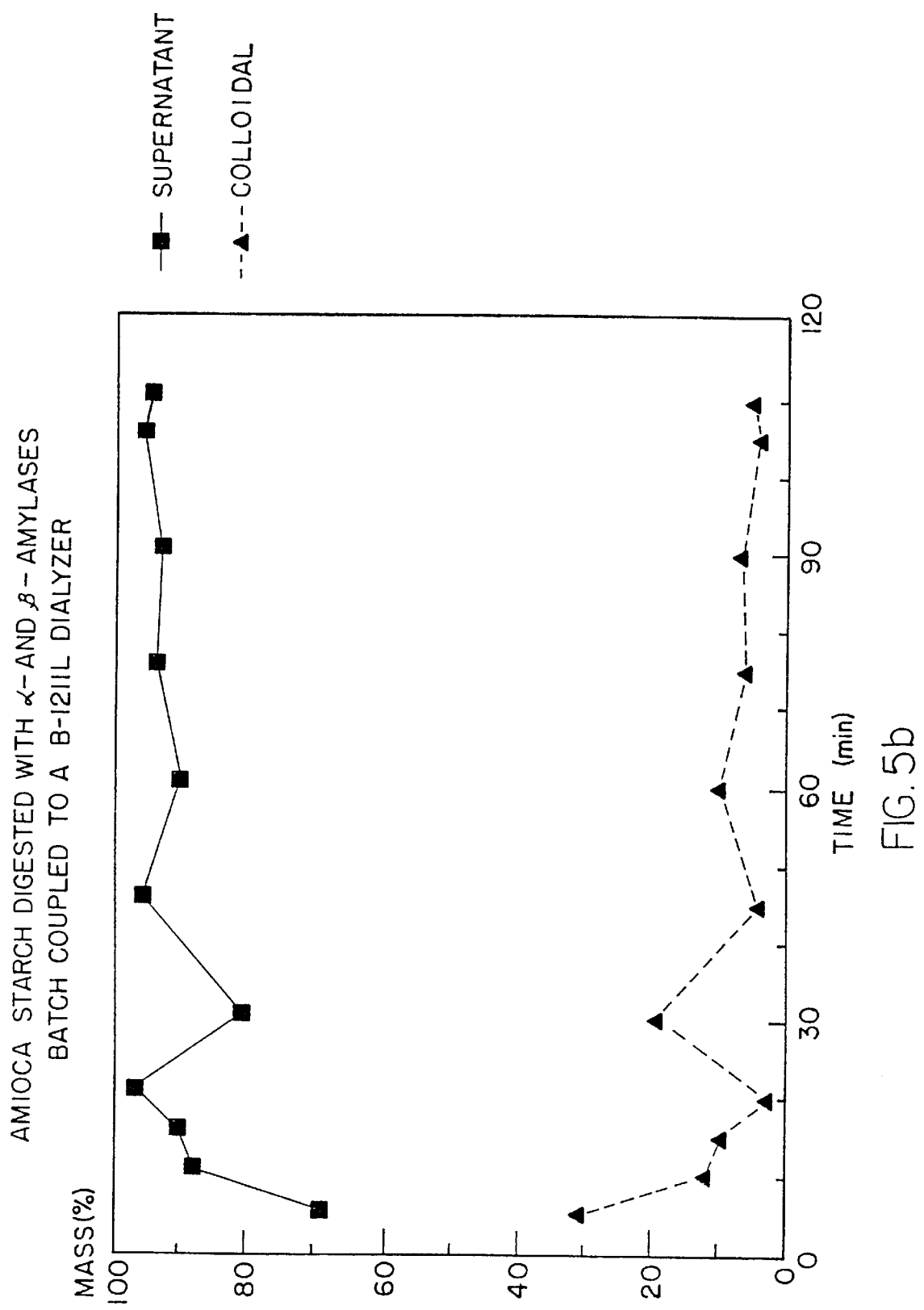

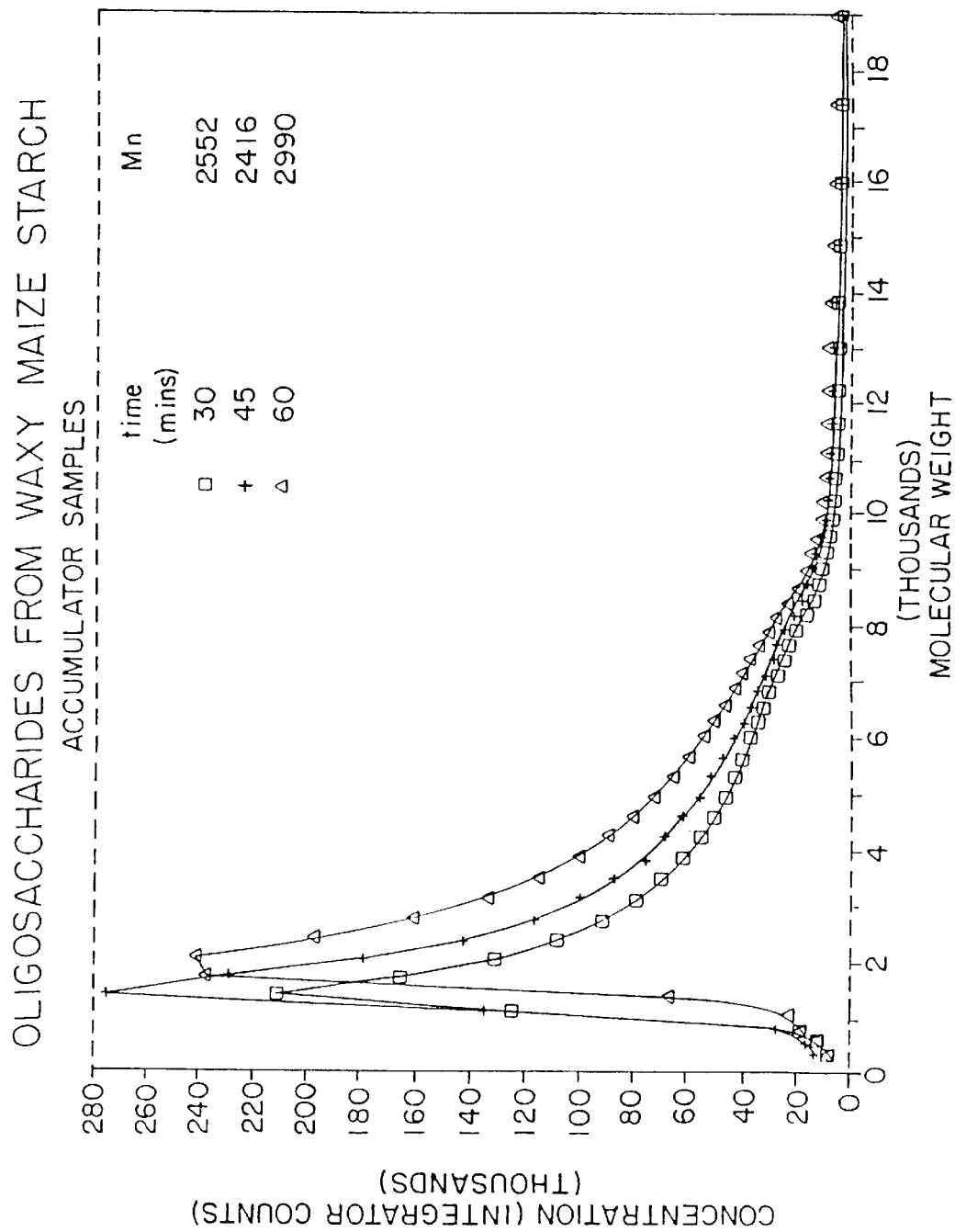

OSMOTIC AGENTS FOR PERITONEAL DIALYSIS

This is a divisional of application Ser. No. 182,708, filed on Apr. 18, 1988 now U.S. Pat. No. 5,039,609 which is a continuation-in-part of Ser. No. 774,261 filed Sep. 10, 1985 now abandoned.

FIELD OF THE INVENTION

The present invention relates to a novel method of performing peritoneal dialysis. More specifically, it relates to the use of relatively low molecular weight peptides as osmotic agents in a peritoneal dialysate.

Another aspect of the present invention relates to an improved method for the enzymatic hydrolysis of proteins to produce low molecular weight peptides for use in peritoneal dialysis.

In still another aspect of the present invention the novel process may be applied to the enzymatic hydrolysis of oligosaccharides such as starch to produce products free of enzymes, high molecular weight starch fractions and insoluble starch material. If desired, this novel process may also be applied to glucose as well.

BACKGROUND OF THE INVENTION

The normal function of the mammalian kidney includes such activity as maintaining a constant acid-base and electrolyte balance, removing excess fluids and removing undesirable products of the body's metabolism from the blood. In an individual with end stage renal disease, this functioning of the kidney may be reduced to as low as 5% or less of the normal level. When renal function has decreased to this point, artificial means must then be employed to substitute for the kidney activity, if life is to be sustained. This is accomplished clinically by the use of dialysis. One of the most common methods for achieving this is hemodialysis, in which the patient's blood is passed through an artificial kidney dialysis machine. In the machine, a synthetic non-permeable membrane acts as an artificial kidney with which the patient's blood is contacted on one side; on the opposite side of the membrane is a dialyzing fluid or dialysate, the composition of which is such that the undesirable products in the patient's blood will naturally pass across the membrane by diffusion, into the fluid. The blood is thus cleansed, in essentially the same manner as the kidney would have done, and the blood is returned to the patient's body. This method of dialysis requires the patient to be physically "hooked up" to the machine for several hours, often several times a week. For obvious reasons, this technique, although efficient, presents a number of inconveniences.

Some of the disadvantages associated with hemodialysis, which requires extracorporeal treatment of the blood, are overcome by the use of techniques which utilize the patient's own peritoneum as the required semipermeable membrane. The peritoneum is the membraneous lining of the body cavity which contains large numbers of blood vessels and capillaries and is thus capable of acting as a natural semipermeable membrane. Dialysis solution is introduced into the peritoneal cavity, via a catheter in the abdominal wall. A suitable period of residence time for the dialysate is allowed to permit the exchange of solutes between it and the blood; fluid removal is achieved by providing a suitable osmotic gradient from the blood to the dialysate to permit water outflow from the blood. Thus, the proper acid-base, electrolyte and fluid balance is returned to the blood and the dialysis solution is simply drained from the body cavity through the catheter. Although more than one type of peritoneal dialysis exists, the technique known as continuous ambulatory peritoneal dialysis (CAPD) is particularly favored, since it does not require the patient to remain tied to machinery while the solute and fluid exchange is accomplished. The only sedentary period required is during infusion and draining of the dialysis solution.

One of the most difficult aspects of peritoneal dialysis, and yet one of the most important, is finding a suitable osmotic agent for inclusion in the dialysate, by which the required osmotic gradient would be achieved. By osmotically active agent, as used herein, is meant a substance present in the dialysis solution which is capable of maintaining the osmotic gradient required to cause transport of water and toxic substances across the peritoneum into the dialysis solution. The appropriate agent should fulfill at least two critical criteria. First, it must be, to a greater or lesser extent biologically inert, i.e., non-toxic and yet metabolizable, and second, should preferably not rapidly cross the peritoneal membrane into the blood; this would allow maintenance of the maximum ultrafiltration gradient, and also would prevent toxicity or accumulation of unwanted substances in the blood. Absence of toxicity is particularly important, since nearly any substance placed in the peritoneum will eventually find its way into the circulation, whether by a slow lymphatic drain, or by dialysis across the peritoneal membrane. To date, no known substance has completely satisfied these needs, although a number of different materials have been used with varying success. The agent which has currently achieved the most widespread acceptance is glucose. Glucose has the advantage of being non-toxic, and is so readily metabolizable if it enters the blood. The major problem with its use, however, is that it is readily taken up into the blood from the dialysate. Although, as noted above, any substance will eventually find its way into the circulation, glucose crosses the peritoneum so rapidly that the osmotic gradient is broken down within 2–3 hours of infusion. This may even cause a reversal of the direction of ultrafiltration, causing the unwanted result of water being reabsorbed from the dialysate toward the end of the time allowed for exchange. Further, the amount of glucose which is taken in may represent a large proportion of the patient's energy intake, possibly being as high as 12–35%; while this does not significantly affect a non-diabetic patient, it can be a severe metabolic burden to a patient whose glucose tolerance is already impaired. This added burden may be implicated in the hyperglycemia and obesity, observed in a number of CAPD patients. Diabetic patients suffer from the further inconvenience and risk of having to add insulin to the peritoneal dialysate, in order to reduce the risks of hypoglycemina resulting from the added glucose load.

Use of glucose also presents problems in the preparation of the dialysate. Sterilization of the dialysate is typically accomplished by heating which, at physiological pH, will cause glucose to caramelize. To compensate for this, the pH of the dialysate is usually adjusted to within the pH range of 5.0–5.5. This low pH, so far below that which is normal for the body, may be responsible for the pain experienced by some patients on inflow, and could also cause sclerosis of the peritoneal membrane, which will in turn cause a decrease in solute clearance (Schmidt, et al., *Arch. Int. Med.*, 141: 1265–1266, 1980).

These disadvantages make the finding of a suitable alternative to glucose as an osmotic agent highly desirable. A number of substances have been proposed to meet the criteria of being biologically inert, not readily crossing the peritoneal membrane, being non-toxic and exerting adequate osmotic pressure a flow concentrations. To date, none of the suggested materials has proven to be an adequate substitute for glucose. For example, the use of dextrans (Gjessing, *Acta Med. Scan.*, 185: 237–239, 1960) or polyanions (U.S. Pat. No. 4,339,433) has been proposed because of their high molecular weight, which should minimize their diffusion across the peritoneum into the blood. However, the role of the lymphatic system in the process of solute transport apparently limits the advantages of the high molecular weight per se (Allen, et al., *Amer. J. Physiol.*, 119: 776–782, 1937). Also, with respect to the polyanions, it is unclear as to what the toxic effects of these would be, since most are non-metabolizable. Similar problems with metabolism are observed with compounds such as sorbitol, xylitol and glucose polymers. Sorbitol which is very slowly metabolized has been associated with instances of hyperosmolar coma and death (Raja, et al., *Ann. Int. Med.*, 73: 993–994, 1970), and is no longer used. Both xylitol and glucose polymers also have a tendency to accumulate in the blood, and may be associated with unpleasant side effects (Bazyato, et al., *Trans Amer. Soc. Artif. Interm. Organs*, 28: 280–286, 1982). Fructose, which is comparable to glucose in its osmotic capacity, also exhibits many of the same disadvantages; because of its higher cost, it has not achieved widespread use.

More promising is the proposed use of amino acids to replace glucose. Amino acids are well-tolerated, with no known adverse side effects (Oren, et al., *Perit. Dial. Bull*, 3: 66–72). Because of their lower molecular weight, they exert a higher osmotic effect, on a mass basis, than glucose. This also probably results, however, in a more rapid uptake into the blood, causing a rapid loss of osmotic gradient. Although, unlike glucose, amino acid uptake may be beneficial, in that it may compensate for the protein loss observed in many CAPD patients, there is a considerable disadvantage in the almost prohibitive costs of amino acid solutions when compared with glucose. Furthermore, the rapid uptake of amino acids results in a considerable nitrogen burden, with a significant increase in blood urea nitrogen levels. Thus, it appears that even amino acids do not provide the appropriate substitutes.

The present invention, however, now provides improvement in the method for peritoneal dialysis which employs an osmotic agent which is not only a safe and beneficial alternative to glucose, but which also is economically feasible. It has now been unexpectedly discovered that a mixture of relatively low molecular weight oligopeptides (300–2000 daltons) derived from the enzymatic hydrolysis of a high quality protein, such as whey protein, may be used as an effective osmotic agent in a peritoneal dialysis solution; in comparison with an amino acid solution, the somewhat higher molecular weight of the peptides prevents the rapid uptake into the blood, allowing a more effective maintenance of the osmotic gradient as well as preventing the unwanted increase of nitrogen in the blood. The peptide mixture, which is ultimately, although very slowly, absorbed into the serum further provides a valuable dietary supplement, being derived from high-quality protein. Finally, the present peptide mixture provides an inexpensive and easily obtainable source of osmotic agent. Other peptide mixtures, used for medicinal purposes, have been previously described. For example, U.S. Pat. No. 4,427,658 describes a protein hydrolysate derived from enzymatic hydrolysis of whey protein. In that case, nearly total enzymatic hydrolysis was claimed to be performed, with no separation of larger from smaller peptides. Therefore, the resulting product apparently contains peptides of much larger sizes, possibly up to 5000 daltons or more, in the final mixture. These may pose antigenic and/or allergic risks since pinocytotic uptake from the peritoneum to the blood is known. This is significantly different from the carefully separated, relatively low molecular weight mixtures of the present invention.

BRIEF DESCRIPTION OF THE INVENTION

The present invention relates to a composition useful in peritoneal dialysis which comprises an osmotically effective amount of a mixture of peptides, the mixture substantially consisting of peptides having a molecular weight of between 300–2000 daltons, and equivalent weight between 150–1500, in combination with an electrolytically osmotically-balanced peritoneal dialysis solution.

It also relates to a method of peritoneal dialysis which comprises administering to a patient in need of dialysis a therapeutically effective amount of a peritoneal dialysate comprising an osmotically effective amount of the low molecular weight peptides as noted above.

It further relates to a peritoneal dialysate which comprises as an osmotically active agent the above-mentioned mixture of small peptides.

The present invention also provides a method for the isolation of low molecular weight solutes which comprises contacting the aqueous solution with one side of a dialysis membrane capable of allowing the transport of the solutes, simultaneously contacting the opposite side of the membrane with substantially pure water derived from a reverse osmosis unit fed from a reservoir, the water having a sufficient solute concentration to allow transport of the solutes across the membrane into the water, directing the water and transported solutes to the reservoir, and accumulating transported solutes in the reservoir by solute retention of reverse osmosis membrane.

As indicated earlier, the present invention also provides a novel process for the enzymatic hydrolysis of proteins and oligosaccharides.

BRIEF DESCRIPTION OF THE DRAWINGS

FIGS. 5A and 5B show the decrease in both supernatant and sedimentary carbohydrate in the membrane reactor vessel.

FIG. 6 shows the molecular weight distribution of the oligosaccharides formed by enzymatic cleavage and transferred into the RO accumulator circuit.

DETAILED DESCRIPTION OF THE INVENTION

Figure 1:
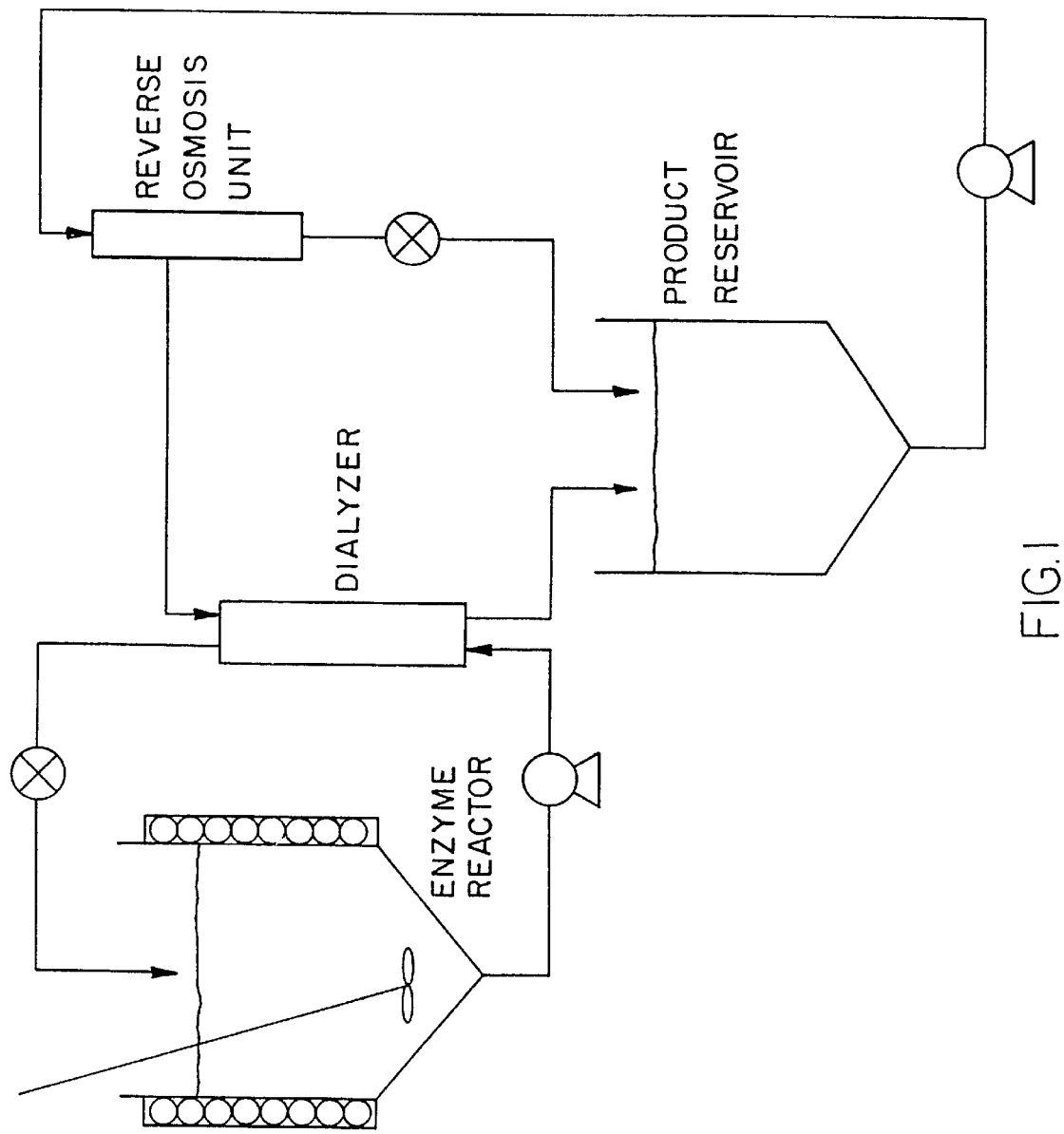
FIG. 1 shows a diagrammatic representation of the combined dialysis-reverse osmosis scheme of isolation.

The present pharmaceutical compositions contain as the active osmotic agent, peptide fractions of differing molecular weight distributions, each peptide having an upper molecular weight cut-off of 2000 daltons. Generally speaking, the peptides' amino acid compositions are not particularly important, and, of course, will vary according to the source protein from which the mixture is derived. The most important feature is the selection of a low molecular weight population, which must be large enough to prevent rapid transport across the peritoneal membrane, and yet small enough to maintain the required osmotic gradient, as explained above. It has been determined that the most effective size range of the included peptides is about 300–2000 daltons; the equivalent weight should be between about 150–1500, with the preferred average equivalent weight being between about 250–750.

The peptide mixtures may be readily prepared by hydrolysis of larger proteins. Protein hydrolysis may be accomplished by a number of known methods. For example, a common hydrolysis technique is boiling the protein in the presence of strong mineral acids or alkalis. This has the unfortunate effect, however, of potentially destroying or at least altering a number of the liberated amino acids. It also is difficult to control the product which is produced; acid hydrolysis will not necessarily break the protein in the same position in every case and thus results in an unpredictable product. The reaction is also quite rapid, and unless carefully monitored, will result in collection of individual amino acids rather than the desired mixture of small peptides. Thus, acid hydrolysis is not deemed suitable for the present purpose. A second possibility for hydrolytic tools are a number of chemical reagents, such as hydroxyamine or 2-nitro-5-thiocyano benzoate, each of which will cleave a protein only at specific parts in the chain. The preferred choice is the use of enzyme hydrolysis to yield the desired peptide mixtures. Enzyme hydrolysis has the important advantage of being relatively easy to control, so that complete hydrolysis does not occur, and the product is of the desired molecular weight composition.

There is a broad selection of enzymes from which a suitable hydrolytic agent may be chosen. Some of the possible choices are, among others, trypsin, chymotrypsin, papain, pepsin, or certain microbial proteases. A mixture of proteolytic enzymes, such as pancreatin (chymotrypsin and trypsin), may also be used. Each of these generally cleave protein at a specific site; for example, trypsin will cleave a protein only at the carboxyl side of lysine and arginine residues. Chymotrypsin will preferentially attack at the carboxyl side of an aromatic amino acid. Pepsin prefers to cleave hydrophobic amino acids. The various specificities of other proteolytic enzymes is well known and readily available to the experienced chemist. Because of this specificity, the end-product peptide mixture will differ depending, at least in part, on which enzyme is used for hydrolysis. However, as is demonstrated below, the actual composition of the peptide mixture is of little or no importance, provided the proper osmolality is obtained, and the peptides are within the desired size range. It will be readily apparent to one skilled in the art which types of enzymes are useful for the present purpose.

Another variable which affects the type of product produced is, of course, the type of protein which is hydrolyzed. Although virtually any type of dietary protein is a suitable substrate, it is preferred that the protein used is a high quality protein. By the term high quality protein, as used in the present specification and claims, is meant a protein which contains a high proportion, generally 30 at least 50%, and preferably in the range of 60% to 70%, of the essential amino acids, i.e., lysine, leucine, isoleucine, methionine, phenylalanine, threonine, tryptophan, valine and histidine. Generally speaking, animal protein tends to be of a higher quality in this sense than vegetable protein; particularly good sources of high quality protein are collagen, certain bovine milk proteins, such as whey, and egg protein, particularly ovalbumin, although any protein which supplies the appropriate proportions of amino acids is useful. However, certain types of protein, such as casein, which contain a high percentage of phosphorus, are not appropriate substrates because of the necessity of limiting phosphorus intake in uremia. The reason for a preference for high grade protein is that, although the peptides do not, as do amino acids, readily diffuse across the peritoneal membrane, some diffusion is inevitable. Since at least some of the peptides in the mixture will eventually pass into the bloodstream it is desirable to insure that what does enter is of nutritional value. The dialysate thus serves also, to some extent, as a parenteral feeding supplement, should diffusion across the membrane occur.

The most preferred protein substrate for peptide production is milk whey protein. Whey protein is the material which remains in solution following the acidification of milk, i.e., after the precipitation of the phosphoprotein casein. Whey protein is made up primarily of β-lactoglobulin, α-lactalbumin, immunoglobulin and bovine serum albumin with over 60% being composed of the β-lactoglobulin and α-lactalbumin fractions. The amino acid composition of these two proteins is well known, as shown in Table 1. Whey protein has the advantages of being both easily obtainable and relatively inexpensive to produce.

TABLE 1

AMINO ACID COMPOSITION OF β-LACTOGLOBULIN AND A α-LACTALBUMIN

| β-LACTOGLOBULIN | | α-LACTALBUMIN |
|---|---|---|
| 9 | Asp(D) | 13 |
| 4 | Asn(N) | 8 |
| 3 | Asx(B) | — |
| 8 | Thr(T) | 7 |
| 7 | Ser(S) | 7 |
| 9 | Glu(E) | 8 |
| 9 | Gln(Q) | 5 |
| 7 | Glx(Z) | — |
| 8 | Pro(P) | 2 |
| 3 | Gly(G) | 6 |
| 14 | Ala(A) | 3 |
| 5 | Cys(C) | 8 |
| 10 | Val(V) | 6 |
| 4 | Met(M) | 1 |
| 10 | Ile(I) | 8 |
| 22 | Leu(L) | 13 |
| 4 | Tyr(Y) | 4 |
| 4 | Phe(F) | 4 |
| 2 | Try(W) | 4 |
| 15 | Lys(K) | 12 |
| 2 | His(H) | 3 |
| 3 | Arg(R) | 1 |

The individual whey proteins are readily isolatable by virtue of their fractional solubility in ammonium sulfate solution. A number of schemes exist for separation of the protein from various substances by its solubility in 264 g/l of ammonium sulfate (see, for example, Armstrong, et al., *Biochem. Biophys. Acta*, 147: 60–72, 1967; Aschaffenberg, et al., *Biochem. J.*, 65: 273–277, 1957; Cervone, et al., *Biochem. Biophys. Acta*, 295: 555–563, 1973). Alternately, it is also possible to obtain the individual whey proteins commercially (Sigma); or as mixed protein concentrates (Express Foods).

It will be immediately clear to the skilled chemist as aforesaid, that the actual peptide composition will vary according to the source of the protein and the enzyme used for hydrolysis. The enzyme is controlling because, as noted above, each enzyme attacks the protein at a specific amino acid or acids. Thus, the use of, for example, trypsin, will produce the same group of small peptides with each use, provided the substrate is the same. Therefore, given a controlled set of reaction conditions, it will always be possible to produce a predictable peptide mixture using the same pure enzyme and the same starting protein. It is true that most commercial enzymes may be contaminated with small amounts of other proteases. These contaminants may be responsible for the production of considerable amounts of free amino acids, if the peptides are allowed to remain in contact with the enzyme. Removal of peptides in the desired size from the reactor as they are produced avoids the problem of production of unwanted amino acids to a large extent. It will be readily understood, in fact, that the actual composition of the peptide mixture, at least with respect to what peptides are present, is to a large extent irrelevant. The critical factor is ensuring that the size of the peptides produced is maintained within the prescribed 300–2000 dalton limit.

As noted above it is important to monitor the hydrolytic process as it proceeds, in order to ensure that the hydrolysis yields the appropriate molecular weight peptide compositions. This is easily done because of the relative slowness at which the enzymatic process proceeds, but to insure further that significant amounts of amino acids do not become part of the mixture, the reaction may be run at a temperature and/or pH which is other than optimum for the enzyme being used, so that the rate of enzyme cleavage is kept very low. The conditions required to produce the desired mixture will necessarily be varied depending on the enzyme employed. Since enzymatic hydrolysis of protein is such a well-known procedure, the conditions required for optimum proteolysis using any number of different enzymes is readily available in the literature (see, for example, U.S. Pat. Nos. 4,427,658 and 4,145,445 for just a few of the known procedures). It is within the ability of the average chemist, without undue experimentation, to select the procedure which is best suited to the substrate and enzyme being used given the available information.

Although the present invention may, as noted, employ any proteolytic enzyme, or combination of enzymes, a particularly preferred enzyme is pancreatin, or alternately, its component enzymes, chymotrypsin and trypsin. In order to further reduce the problem of obtaining excessive amounts of amino acids because of the potentially contaminating proteases, the ratio of enzymes to substrate should be kept fairly low, within the range of 0.5% to a maximum of about 5.0%. After the hydrolysis procedure is completed, and the desired peptide combination is obtained, the peptides may be purified and separated from the reaction mixture by a number of different methods. To a large extent, the final molecular weight range will also be dependent on the method of separation employed, as noted below.

The preferred products of the present invention are therapeutic compositions comprising a mixture of peptides produced by enzymatic hydrolysis of a high quality protein, the mixture having the following characteristics:

a) the mixture consists substantially of peptides having molecular weights of between 300 and 2000 daltons;

b) the mixture contains no more than 5 mole percent of free amino acid;

c) the mixture contains at least 50% essential amino acids in peptide form;

d) the mixture is osmotically effective when added in sufficient amount to a peritoneal dialysate solution; and e) the mixture has a component equivalent weight of between about 150 to 1500.

Particularly preferred compositions are those in which the high quality protein is whey protein, which is hydrolyzed by a combination of trypsin and chymotrypsin, and the final mixture has an essential amino acid content of about 60–70%. These compositions may be used therapeutically as the osmotic agents in peritoneal dialysis solutions, as noted above, but because of their high levels of essential amino acids, may also be employed as part of a parenteral feeding supplement.

As the foregoing discussion makes clear, the characteristic of the final product which is most important is that the peptides contained in the solution be within a very specific molecular weight range, i.e., between about 300 to about 2000 daltons. The equivalent weight of the peptide molecules, which is the expression of the molecules' molecular weight relative to the charge on the molecule, is preferably in the range of 150 to 1500. The charge on the molecules contributes to the overall osmotic coefficient of the mixture and solution. Molecules of greater molecular weight than 2000 daltons create very little osmotically induced ultrafiltration, and very small molecules leak too quickly into the circulation. It is thus important that it be possible to control the hydrolytic reaction and the resultant product in some manner which will assure that the required molecular weight range be obtained.

A number of different methods exist in the art for isolating and/or purifying the peptide components of a solution. For example, trichloroacetic acid (TCA) may be used to precipitate whatever remaining protein and enzyme there is in the reaction solution. Alternately, a water-miscible protein precipitating solvent, such as acetonitrile (ACN) protein precipitates at about 35–45% ACN with the peptides remaining in solution. Further, one may use the volume exclusion method, adding polyethylene oxide to cause a phase separation. However, none of these methods can assure that the exact product desired, i.e., a peptide mixture of specific molecular weight composition, will be obtained.

Ultrafiltration is a technique which is most frequently employed when a final product of specific molecular weight is desired. However, ultrafiltration also has a severe disadvantage associated with it, in that reliable separation cannot be obtained unless there is at least about a ten-fold difference in molecular weight of the components to be separated. In fact, when experimentally employed in connection with resolution of the present product, it was routinely found that molecules of molecular weight much higher than 2000 daltons would appear in the final solution, regardless of the chosen 2000 molecular weight cut-off of the ultrafiltration filter (see Example 2). Quite simply, then, there is not currently available any reliable method for directly isolating low molecular weight products from a parent mixture which is heterogeneous in the molecular sizes of its components.

In connection with the preparation of the present osmotic agents, however, a system for the isolation of low molecular weight solutes from a heterodisperse molecular weight mixture has been developed. The present method, which is based on the simple but unexpected combination of dialysis and reverse osmosis, has proven to be particularly amenable to the peptide separation required for the present product. However, its use is not limited to peptides; it may, in fact, be used for separation of virtually any type of low molecular weight solutes as, for example, starch or glucose as indicated hereinbefore. By "low molecular weight", as used in the present specification and claims, is meant molecules of about 5000 daltons or less in size.

In general terms, the process, diagrammatically represented in FIG. 1, proceeds as follows: the aqueous solution containing the solutes to be isolated is perfused through a dialyzer unit and is returned to the source reservoir ("reactor" of FIG. 1). The dialyzer membrane is washed on the opposite side from the aqueous solution with a stream of fresh water provided by a reverse osmosis unit. The reverse osmosis unit produces, under pressure, a supply of substantially pure water, providing a sufficient concentration gradient to allow the dialysis of the relatively concentrated solutes across the membrane and into the stream. Since species with a molecular weight greater than 2000 daltons do not generally dialyze at a significant rate across a dialysis membrane, these larger species will remain in solution and be returned to the source reservoir, while low molecular weight (less than 2000 daltons) product will pass into the fresh water stream and flow into the reverse osmosis reservoir. When the fluid from the reverse osmosis reservoir is pressurized, the reverse osmosis element permeates only pure water which is, in turn, contacted with the dialyzer membrane where it will again accumulate the dialyzable, low molecular weight species and transport them to the reverse osmosis reservoir where they are concentrated. The process may be continued until such a time as the back. osmotic pressure in the reverse osmosis reservoir significantly impedes the production of fresh water, or until the source material is used up. The concentrated products so produced may then be further isolated by known methods, or used as is, depending on the requirements.

The principles behind both the dialysis process and the reverse osmosis process are well known and need not be discussed in great detail here. Reverse osmosis is routinely used for purification of water (see, U.S. Pat. No. 3,774,763) and can be characterized as a process in which high pressure on a concentrated solution allows passage, through a semipermeable membrane, of the solvent from the concentrated solution to a more dilute fluid (e.g., water or air). This procedure simultaneously purifies the solvent and isolates the solutes contained therein. Dialysis may be defined as a passive process in which the result is the transfer of solute molecules from a liquid having high solute concentration to a liquid having low solute concentration, via transport of the solutes across a membrane separating the two liquids. The use of dialysis alone is to a large extent presently limited to the separation of very small molecules from very large molecules, as in the case of hemodialysis.

Various membrane separation methods have been previously combined to achieve different ends. For example, U.S. Pat. No. 3,472,765 applies a combination of reverse osmosis and ultrafiltration for the separation of microorganisms in a biological reaction system from their carrier liquid or their desirable metabolic products. This method, to a large extent, relies upon the presumed molecular weight cut-off of the ultrafiltration membranes. Similarly, U.S. Pat. No. 4,000, 065 combines reverse osmosis and ultrafiltration to purify aqueous solutions containing low levels of organic contaminants which may have molecular weights of less than 10,000. This method depends a great deal on the limited solubility ranges of the contained contaminants and also relies heavily on ultrafiltration to produce the desired result. Each of these processes claims to be able to separate out small molecular weight substances from aqueous solutions; however, neither describes a separation procedure in which a product containing a narrow range of low molecular weight solutes can be separated from other solutes which are very close in molecular weight. The further unreliability of the ultrafiltration membrane cut-off points has been previously discussed. Thus, neither of these procedures would appear to be suitable for producing the present product. U.S. Pat. No. 3,774,763 describes a method of water purification using reverse osmosis, said purified water being then possibly used for a hemodialysis unit. However, the reverse osmosis procedure is complex, requiring a number of additional elements such as deionizers, and further, once the water is purified, there is no continued interaction with a dialysis unit.

The novel process described herein, however, does not require that the solutes be of low solubility in the aqueous solution, nor does it involve the disadvantages associated with the ultrafiltration procedures. Instead, the present process utilizes the inherent limitations of the dialysis procedure to an advantage, to separate out from a heterogeneous mixture of compounds which may be very close in molecular weight, molecules of 2000 daltons or less, and augments the separation with use of a reverse osmosis process to both provide a continual source of pure water for the dialysis procedure and to continuously accumulate the dialyzable product in concentrated form in the reverse osmosis reservoir. The final product yielded is one which meets the requirements of a solution containing a specified range of low molecular weight peptides. The process is simple, requiring essentially only a two-step procedure which can be repeated continually until the concentration of solute in the reverse osmosis reservoir is such as to prohibit the production of sufficient pressure to continue the reverse osmosis step. The process has the further advantage of not necessarily requiring any further separation or purification procedures upon its completion.

The elements to be used in the present procedure may be any dialysis and reverse osmosis apparatus known in the art. Each unit may also be operated in accordance with known procedures with respect to temperature, pressures, feed rates, and so on. The operating pressure in the dialyzer should generally be no more than 500 mm, preferably less. The operating pressure for the high pressure portion of the reverse osmosis unit must be in excess of the osmotic pressure of the solution in the reverse osmosis reservoir and must be sufficiently elevated so as to produce a fresh water permeate stream against which the solute containing stream from the reactor is dialyzed. The typical operating pressure of the reverse osmosis unit in production of the present product is between 150 and 300 psi, and preferably between 200 and 250 psi; however, it will be apparent to the experienced worker that the pressure may be varied in accordance with product to be isolated, if it is other than small peptides. Suitable connections for the two units are any type of low pressure tubing composed of an inert, non-toxic material such as plastic or silicon. The exception is the connection between the pump and circulating line of the reverse osmosis which requires high pressure plastic lines.

A wide variety of membranes suitable for use in dialysis and reverse osmosis processes are known in the art (see, for example, Kirk-Othmer Ed., *Encyclopedia of Chemical Technology*, 3rd ed., Vol. 7, "Dialysis", 1979 and Vol. 20, "Reverse Osmosis", 1982). Virtually any of the known membranes with dialytic properties may be employed in dialysis; these may be made of, for example, cellulose, cellulose acetate, ethylene vinyl alcohol, polyacrylonitrile or polymethylmethyacrylate. In the preparation of peptide mixtures, cellulose membranes are preferably used, particularly hollow fiber membranes, and the associated dialyzers. These membranes are available in a range of permeabilities, most of which are suitable for the present procedure. The choice of which membrane to use is made based upon the average size of the desired molecules required. For example, a membrane of "normal" permeability, such as is contained in the HF-140 dialyzer (Cobe Laboratories), is generally impermeable to anything with a molecular weight of over 1500; however, if a slightly larger molecular weight size is desired, certain types of fibers, such as D2-HDF (Enka), are still permeable up to a molecular weight of 3000–4000 daltons. The permeabilities of the commercially available membranes are known, and it is within the skill of the experienced worker to determine which of the membranes is best suited to his purpose, depending on the size and type of molecule to be isolated. With respect to reverse osmosis membranes, any membrane with a high level of retention of electrolytes is suitable. Thin film composite membranes, in a spiral wound configuration, have proven particularly useful in the present process. However, hollow fiber membranes may also be used effectively in the present procedure.

In addition to the choice of membrane, if the source of the solute containing solution is a biological reactor, the average size of the final product mixture may be controlled by limiting the rate of enzymatic cleavage, or the rate of the microbial metabolic process producing the product. For example, when a process of enzymatic cleavage is involved, the rate of the reaction may be kept down by maintaining a low level of enzyme relative to substrate. The rate may also be altered by running the reaction at a temperature or pH which is less than optimum for the enzyme or micororganism bring utilized. Such modifications are well within the ability of one skilled in the art. It will also be apparent to the skilled worker that modifications of the reaction process may be combined with the choice of membrane to most efficiently and accurately produce the desired product. In other words, assuming that the molecular weight of the desired product is known, it is a relatively simple matter to determine, by routine, brief runs through the present procedure, which combination gives the most satisfactory results for the product of interest.

As noted above, the present method is particularly well suited to the preparation of mixtures of low molecular weight peptide mixtures and may be used commercially in connection with hydrolysis of other types of proteins, such as soybean, egg or milk proteins. It may also be readily applied to use with any other heterogeneous, non-peptide mixture from which it is necessary or desirable to isolate low molecular weight species as, for example, it may be applied to the enzyme hydrolysis of polysaccharides such as starch. For example, in many biologically based processes, the desired low molecular weight products are frequently produced in the presence of a number of hormonal and protein contaminants, from which separation of the product presents a serious problem. This can be achieved, for example, in the processing of corn starch hydrolysate to isolate low molecular weight maltodextrins. When corn starch is hydrolyzed enzymatically, the high molecular weight starch is cleaved randomly to produce progressively smaller dextrins. As the process continues, the enzyme activity can be stopped at certain points, to obtain a polydisperse mixture of polyglucoses (maltodextrins) that are used in the food processing industry as baking additives or sweeteners. If the enzyme activity is allowed to continue, the end product is glucose. The use of the present process allows the continuous isolation of maltodextrins of low molecular weight from an enzyme reactor, a procedure which has not been previously possible. Similarly, certain fractions of heparin, an anticoagulant, possess antithrombotic activity without the anticoagulant activity. Although quite valuable, such fractions are difficult to separate from the larger molecule because of their size (about 3000 daltons). The present method provides a means by which the desirable fragment may be readily separated from a heterogeneous mixture of compounds.

With respect to the present product, the purified peptide mixture can be combined with any osmotically balanced aqueous solution appropriate for use as a peritoneal dialysate. Useful dialysate must contain, in order to be effectively osmotically balanced for the present purpose, a concentration of electrolytes sufficient to cause diffusion of water and undesirable metabolic products across the peritoneum. There is no "standard" dialysis solution, since the requirements may vary from one individual to the next. A usual solution would contain, for example, specific quantities of sodium, chloride, lactate, magnesium and calcium. The contents of a typical dialysate solution is presented in Table 2, without the amount of osmotic agent specified; in a glucose solution, glucose monohydrate would typically be added in an amount from about 1.5–4.25%. It will be understood that this represents just one example of a possible solution and that variations in the pattern will be apparent to the skilled artisan. The proportion of the peptide mixture in the dialysate can vary, but normally comprises in the range of about 1 to 15% by weight of dialysate solution. In any event, the amount of peptide used should be sufficient to confer, with supporting electrolytes an osmolality of about 300 to about 500 mOsm/l (280 mOssm/l being normal serum osmolality, and the electrolytes themselves usually contributing an osmolality of about 260 mOsm/l). Administration of the dialysate is achieved in the manner which is usually followed for peritoneal dialysis. Exemplary modes of peritoneal dialysis are described in *Peritoneal Dialvsis*, K. Nolph, ed., Martinus Nighoff Publishers, 1981. The particular treatment regime required by any individual patient is readily determinable by the patient's physician.

TABLE 2

| Components of a typical peritoneal lavage solution (in meq/l) | |
|---|---|
| Na | 132.0 |
| Ca | 3.5 |
| Mg | 0.5 |
| Cl | 96.0 |
| lactate anion | 40.0 |

The present invention may be more clearly understood by reference to the following non-limiting examples:

EXAMPLE 1

The following Example shows a method of preparing the peptide mixture.

A. 150 grams of SAVOR PRO (Express Foods, Inc., Louisville, Ky.), a 75% whey protein concentrate was dissolved in 3 l of distilled water and dialyzed to remove residual lactose and salts. This treatment served to decrease the conductivity of the solution from 700 to 26 micromhos.

The pH of the solution was adjusted to 8.0, and the solution brought to 40° C. The solution was then transferred to an enzyme reactor and circulated through the dialyzer (as diagrammed in FIG. 1). The dialysate side of the dialyzer was supplied pure water from the output of a reverse osmosis (R.O.) unit, utilizing a thin film composite, spiral wound element (Film-Tec). The dialysate was returned to the product reservoir vessel from which the R.O. unit was supplied. The circulation rate through the R.O. from the product reservoir was ten times as great as its pure water production rate, in order to maximize the latter; the unit was operated at a pressure of about 200–250 psi. With both circuits in operation, 1.5 gms. each of Sigma trypsin and chymotrypsin were added to the enzyme reactor. As enzyme cleavage proceeded, the pH of the reaction was maintained by addition of NaOH. As peptides smaller than 2000 daltons formed in the reactor, they were dialyzed through the dialysis membranes (HF-140 hemodialyzer, Cobe Laboratories; Lakewood, Colo.) into the product reservoir, where they remained, since the R.O. unit was retentive of even small electrolytes such as NaCl. The reactor was allowed to run for two hours, with samples taken every 10 minutes.. The product reservoir continued to increase in peptide concentration and osmolality. The final product obtained from the product reservoir was 46.5 grams (31% yield) with an average equivalent weight of 408. Analysis of the product on a $P_2$ gel exclusion column using 30% acetic acid as eluent showed essentially no peptide in the void volume of the resin, indicating all peptides are less than 1800 daltons.

Figure 2:
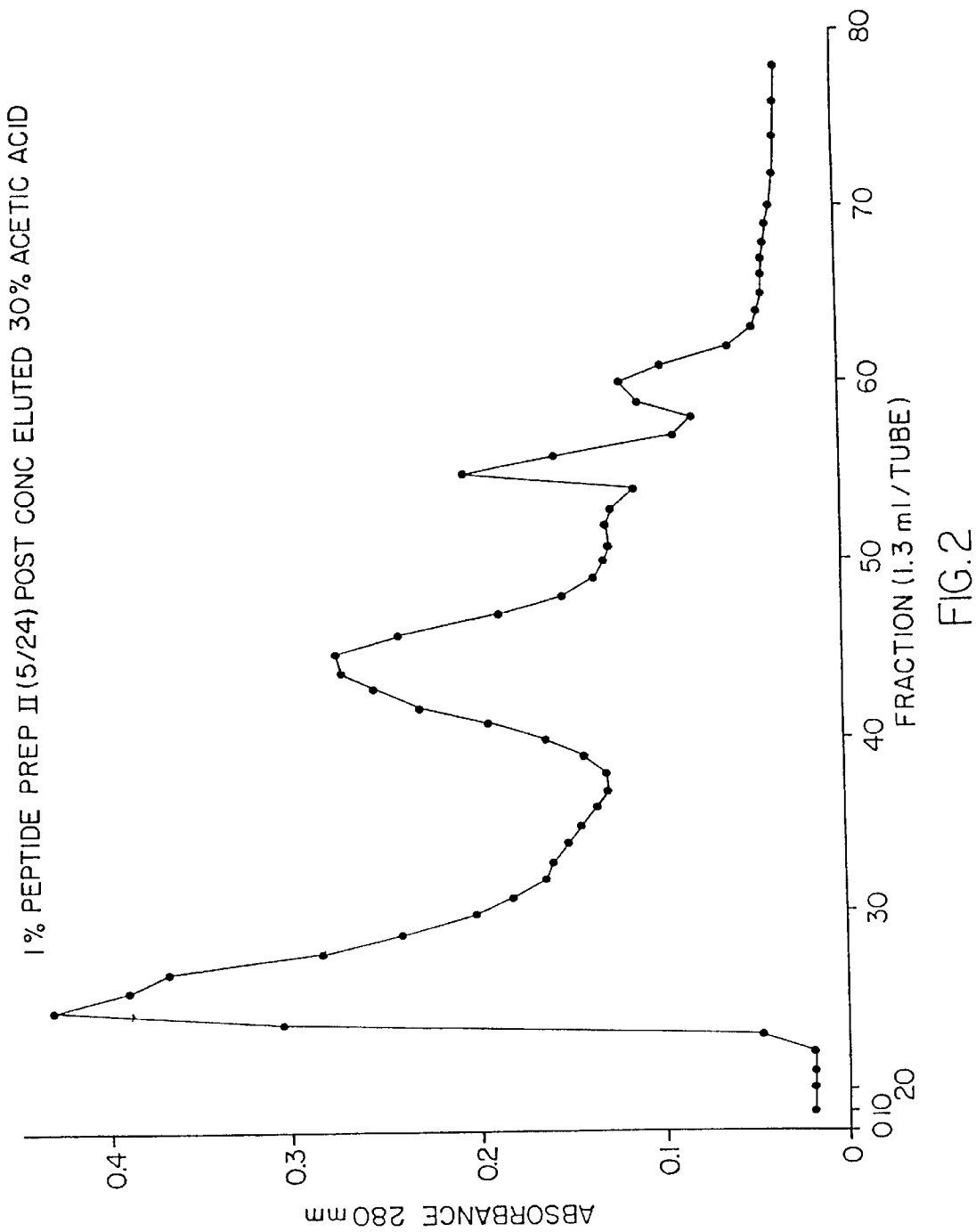
FIG. 2 shows the pattern of elution of the peptide mixture prepared in Example 1B.

B. The reaction of A was repeated exactly, but using a more permeable dialyzer (Fresenius D-6 dialyzer, Bad Homburg, FGR; D2-HDF fibers, Enka AG). This allowed extraction of a higher percentage of larger peptide fragments than was possible in A. The elution was conducted as in A, and the results are presented in FIG. 2. The equivalent weight of the preparation was 483.

EXAMPLE 2

The following Example shows a procedure in which the peptide mixture is purified by ultrafiltration rather than by dialysis and reverse osmosis.

a. A 3% solution of whey protein concentrate (85% protein) was brought to pH=8. Trypsin from Sigma Chem. Co. (#T2395) was added at a ratio of 1:100 on protein after the solution had been brought to 50° C. The osmolality of the starting protein solution (by freezing point depression) was 47 mOsm/l. At the end of 30 mins reaction time the solution was ultrafiltered through a cellulose membrane (limiting cut-off=5000 daltons). When the pH was brought back to the starting value, the osmolality was 112 mOsm/l. Gel exclusion chromatography of the ultrafiltrate indicated that despite the low cut-off designated by the manufacturer a small portion of the starting α-lactalbumin (M.Wt.=14,200 permeated the ultrafilter, in addition to a wide molecular weight range of peptide product.

b. A 5% whey protein solids solution in deionized water was found to have an osmolality of 18 mOsm/l. The solution was dialyzed to reduce electrolyte content and then showed an osmolality of 13 mOsm/l. An ultrafiltrate (through a nominal 20,000 dalton cut-off membrane) of this solution had an osmolality of only 3 mOsm/l while the retentate increased to 19 mOsm/l, indicating that there was very little low molecular weight solute (i.e., lactose, salts, etc.) contributing to the osmolality of the starting whey solution. When the UP retentate was reacted with trypsin at pH=8, the resulting hydrolysate had an osmolality of 59 mOsm/l. The hydrolysate was ultrafiltered through the same type of membrane as above; the filtrate osmolality was found to be 21 mOsm/l. The ultrafiltration experiments showed that the protein digestion was not complete and that the product obtained by ultrafiltration of the hydrolysate contained significant quantities of large peptide fragments. GPC analyses confirmed that the ultrafiltrate contained not only large peptides, but also some of the starting α-lactalbumin.

EXAMPLE 3

The following represent the electrolyte components of the peritoneal dialysate solution used herein (gm/l):

| | |
|---|---|
| NaCl | 5.38 |
| $CaCl_2$ | 0.257 |
| $MgCl_2$ | 0.0508 |
| Na lactate | 4.48 |

The above components provide an osmolality of about 260 mOsm/l. To the above mixture is added 61.1 grams of the peptide mixture per water which provides an osmolality of approximately 126 mOsm/l, giving the solution as a whole an osmolality approximately equivalent to that of a 2.5% glucose solution.

EXAMPLE 4

Utilizing the peptide mixture of Example 1B in a solution as described in Example 3, experiments were carried out to compare the effectiveness of the low molecular weight peptides as osmotic agents relative to the effectiveness of glucose.

The trials employed four rabbits, tested in an A-B sequence, so that each rabbit served as its own control. Each animal was dialyzed with either 2.5% glucose, or alternately, with sufficient peptide to bring the osmolality of the solution to approximately that of the 2.5% glucose solution (385 mOsm/l). Each animal's peritoneal cavity was loaded to approximately 50 ml of dialysate per kg of body weight. The instilled volumes and gain in fluid (due to osmotic ultrafiltration) at the end of 60 minutes are listed in the following table:

| | Glucose Solution | | | Peptide Solution | | |
|---|---|---|---|---|---|---|
| Animal | Vol. ml. t = 0 | Vol. ml. t = 60 | Gain % | Vol. ml. t = 0 | Vol. ml. t = 60 | Gain % |
| #1 | 190.0 | 192.0 | .01 | 204.4 | 232.0 | 13.5 |
| #2 | 142.3 | 161.0 | 12.9 | 139.0 | 164.0 | 18.0 |
| #3 | 175.9 | 189.0 | 7.4 | 183.2 | 200.0 | 9.2 |
| #4 | 168.8 | 177.0 | 5.5 | 157.3 | 172.0 | 9.3 |
| Avg. | | | 6.5 | | | 12.5 |

Figure 3:
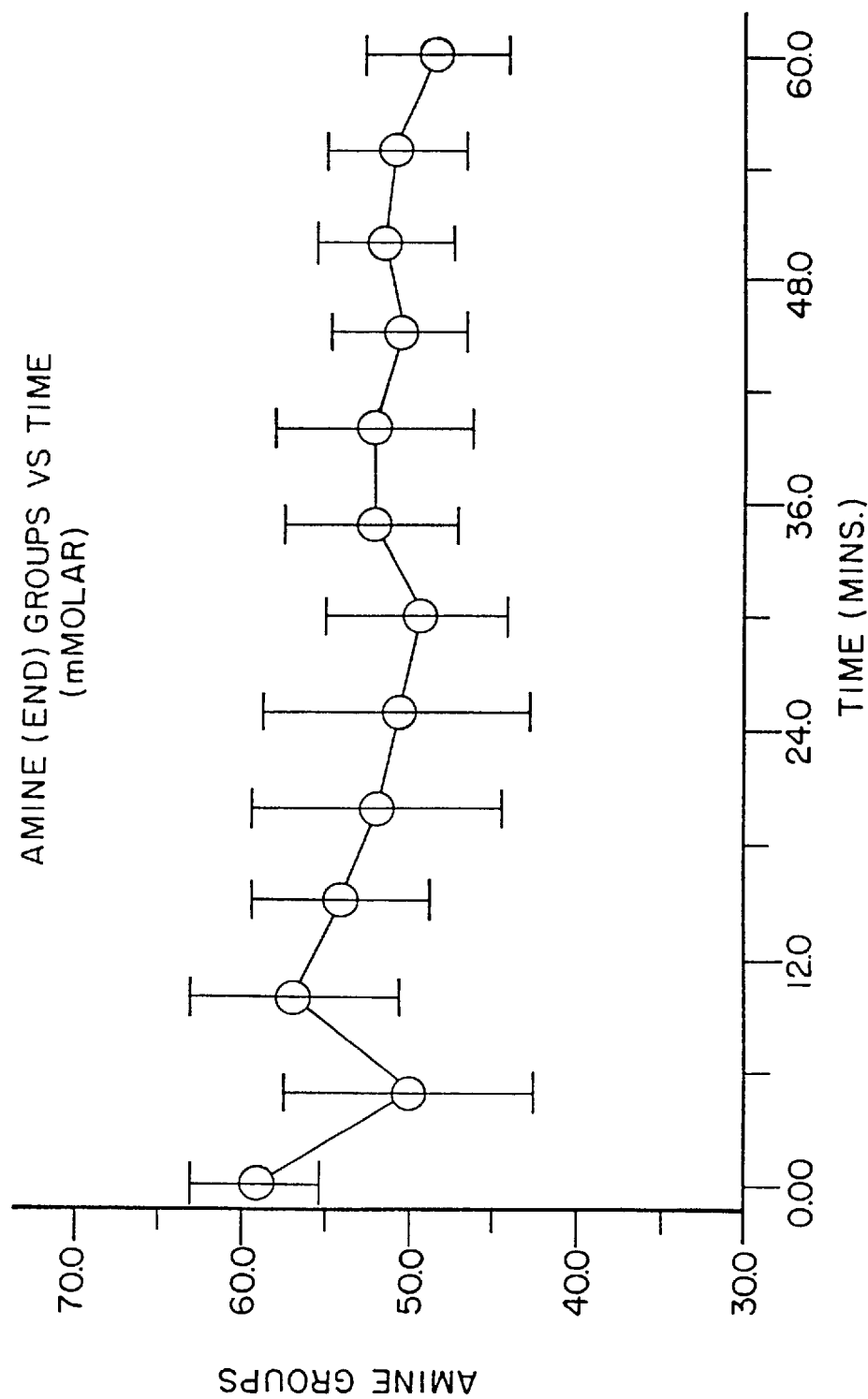
FIG. 3 shows the average amount of peptides, expressed as amine end group, remaining in the peritoneum over a 60-minute period.
Figure 4:
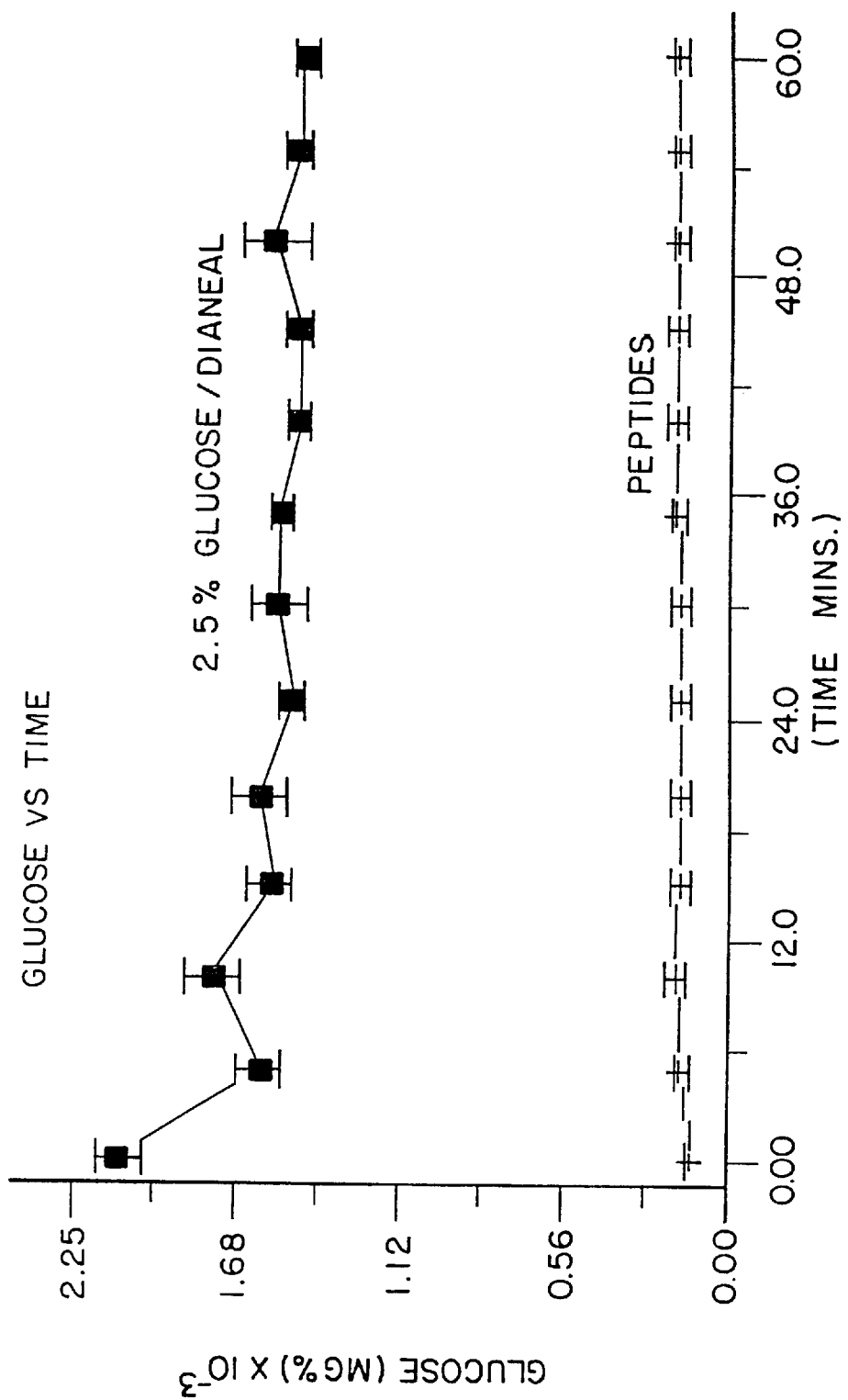
FIG. 4 shows the average amount of glucose remaining in the peritoneum over a 60 minute period.

At the same osmolality as glucose, the peptides show a nearly 100% increase in osmotic pumping activity at 60 minutes, apparently due to the lower rate of loss of peptide compared to glucose in the circulation. FIGS. 3 and 4 show plots of the average amine-end-group concentrations vs. time and the glucose vs. time in the peritoneum. These verify that only 20% of the peptide (measured by end groups) is lost, compared with nearly 35% of the glucose being lost. These results are even more significant in view of the fact that the glucose had not yet equilibrated to plasma levels at 60 minutes.

EXAMPLE 5

The following example shows the application of the described process to the enzymatic hydrolysis of polysaccharides.

A 2% dispersion of Amioca maize starch was prepared by mixing the starch into boiling water and stirring for 15 minutes. The solution was opalescent, indicating the presence of a hydrogel. This dispersion was pumped through the bore of a Baxter 1211L dialyzer at a rate of 200 ml/min, while dialysate (500 ml/min) perfused the outside of the fibers. The dialysate was produced by the R.O. module and high pressure pump as described in Example 1. A mixture of alpha and beta amylase in acetate buffer was added to yield a final concentration in the. starch dispersion of 0.0583 U/ml. Samples were taken from the enzyme reactor tank and the RO accumulator tank for analyses. The enzyme activity in the reactor samples was quenched by addition of 15N NaOH to inactivate the enzyme; supernatant aliquots were isolated from the hydrogel by spinning these samples at 20,000 rpm for 15 minutes. The accumulator samples were free of enzyme activity and required no inactivation. Both sets of samples were analyzed for carbohydrate content by the phenol sulfuric acid assay for reducing sugars and by high pressure liquid chromatography.

Figure 5A:
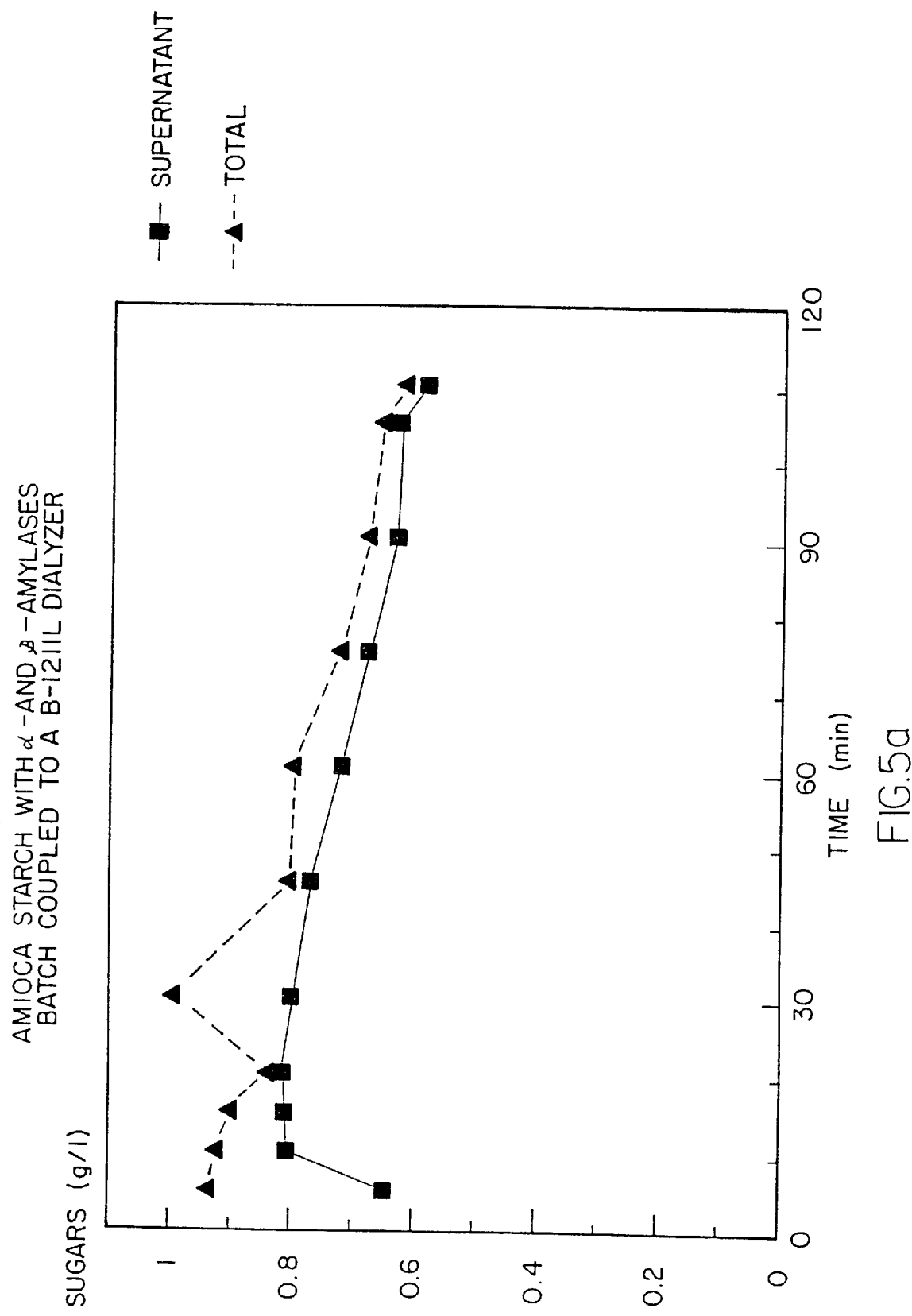

As described earlier, FIG. 5 shows the decrease in both supernatant and sedimentary carbohydrate membrane reactor vessel. Approximately 40% of the high molecular weight starch has been hydrolyzed and transferred out of the reactor system through the dialyzer.

FIG. 6 shows the molecular weight distribution of the oligosaccharides formed by enzymatic cleavage and transferred into the RO accumulator circuit. The oligosaccharides are free of enzymes, high molecular weight starch fractions, and any insoluble starch material.

What is claimed is:

1. A peritoneal dialysis solution which is substantially free of species of molecular weight greater than 2000 daltons and which comprises as an osmotically active agent an osmotically effective amount of electrolytes and a mixture of peptides, the mixture consisting substantially of peptides having a molecular weight of about 300 to about 2000 daltons, and an equivalent weight between about 150 to about 1500, wherein said mixture contains less than 5 mole percent of free amino acid.

2. The solution of claim 1 wherein the peptides are produced by hydrolysis of at least one protein.

3. The solution of claim 2 wherein the protein is a high quality protein containing at least 50% essential amino acids.

4. The solution of claim 2 wherein the hydrolysis is enzyme catalyzed.

5. The solution of claim 3 wherein the protein is a mixture of whey proteins.

6. The solution of claim 5 wherein the enzyme is selected from the group consisting of trypsin, chymotrypsin, pepsin, papain, pancreatin, microbial proteases, and mixtures thereof.

7. The solution of claim 1 wherein the peptides, in combination with electrolytes, are present in an amount sufficient to provide an osmolality of about 300 to about 500 mOsm/l.

8. The solution of claim 1 wherein the peptides comprise about 1 to 15% by weight of the solution.

9. A method of peritoneal dialysis which comprises administering to a patient in need of dialysis a therapeutically effective amount of a peritoneal dialysis solution which is substantially free of species of molecular weight greater than 2000 daltons and which comprises as an osmotically active agent an osmotically effective amount of electrolytes and mixture of peptides, the mixture consisting substantially of peptides having a molecular weight of about 300 to about 2000 daltons, and an equivalent weight of between about 150 to 1500, wherein said mixture contains less than 5 mole percent of free amino acid.

10. The method of claim 9 wherein the peptides are produced by hydrolysis of at least one protein.

11. The method of claim 10 wherein the protein is a high quality protein containing at least 50% essential amino acids.

12. The method of claim 11 wherein the protein is a mixture of whey proteins.

13. The method of claim 10 wherein the hydrolysis is enzyme catalyzed.

14. The method of claim 13 wherein the enzyme is selected from the group consisting of trypsin, chymotrypsin, pancreatin, papain, pepsin, microbial proteases, and mixtures thereof.

15. The method of claim 9 wherein the peptides, in combination with electrolytes, are present in an amount sufficient to provide an osmolality of about 300 to about 500 mOsm/l.

16. The method of claim 9 wherein the peptides comprise between 1 to 15% by weight of the dialysis solution.

17. A pharmaceutical composition which comprises an osmotically effective amount of a mixture of peptides, the mixture consisting substantially of peptides having a molecular weight of about 300 to 2000 daltons, and an equivalent weight of between about 150 to 1500, and less than 5 mole percent of free amino acids in combination with an osmotically balanced aqueous electrolyte solution.

18. The composition of claim 17 wherein the peptides are derived from hydrolysis of at least one protein.

19. The composition of claim 18 wherein the protein is a high quality protein containing at least 50% essential amino acids.

20. The composition of claim 19 wherein the protein is a mixture of whey proteins.

21. The composition of claim 18 wherein hydrolysis is enzyme catalyzed.

22. The composition of claim 21 wherein the enzyme is selected from the group consisting of trypsin, chyomotrypsin, pepsin, papain, pancreatin, microbial proteases and mixtures thereof.

23. The pharmaceutical composition of claim 17 wherein the peptides, in combination with electrolytes, are present in an amount sufficient to provide an osmolarity of about 300 to about 500 mOsm/l.

24. The composition of claim 17 wherein the peptide mixture comprises an amount of 1 to 15% by weight of the aqueous solution.

25. A therapeutic composition comprising electrolytes and a mixture of peptides produced by enzyme catalyzed hydrolysis of a high quality protein containing at least 50% essential amino acids wherein;

a) the mixture consists substantially of peptides having a molecular weight of between 300 to 2000;

b) the mixture of peptides contains no more than about 5 mole percent of free amino acid;

c) the mixture of peptides contains at least about 50% of essential amino acids; and d) the mixture consists substantially of peptides having an equivalent weight between about 150 to 1500.

26. The composition of claim 25 wherein the enzyme is a combination of trypsin and chymotrypsin.

27. The composition of claim 26 wherein the mixture of peptides contains 50–70% of essential amino acids.

* * * * *

UNITED STATES PATENT AND TRADEMARK OFFICE
CERTIFICATE OF CORRECTION

PATENT NO. : 5,869,444  
DATED : February 9, 1999  
INVENTOR(S) : Elias Klein

Page 1 of 1

It is certified that error appears in the above-identified patent and that said Letters Patent is hereby corrected as shown below:

Column 5,  
Line 61, delete --30--.

Column 9,  
Line 22, "back." should read --back--.

Column 12,  
Line 26, "mOssm/1" should read --mOsm/1--.

Column 13,  
Line 10, "minutes.." should read --minutes.--;  
Line 54, "UP" should read --UF--.

Column 15,  
Line 2, "in the. Starch" should read --in the starch--.

Signed and Sealed this

Tenth Day of July, 2001

Attest:

*Nicholas P. Godici*

NICHOLAS P. GODICI  
*Attesting Officer*     *Acting Director of the United States Patent and Trademark Office*